Feb. 21, 1967 R. S. MOORE Plant Pat. 2,717
ROSE PLANT
Filed Oct. 11, 1965
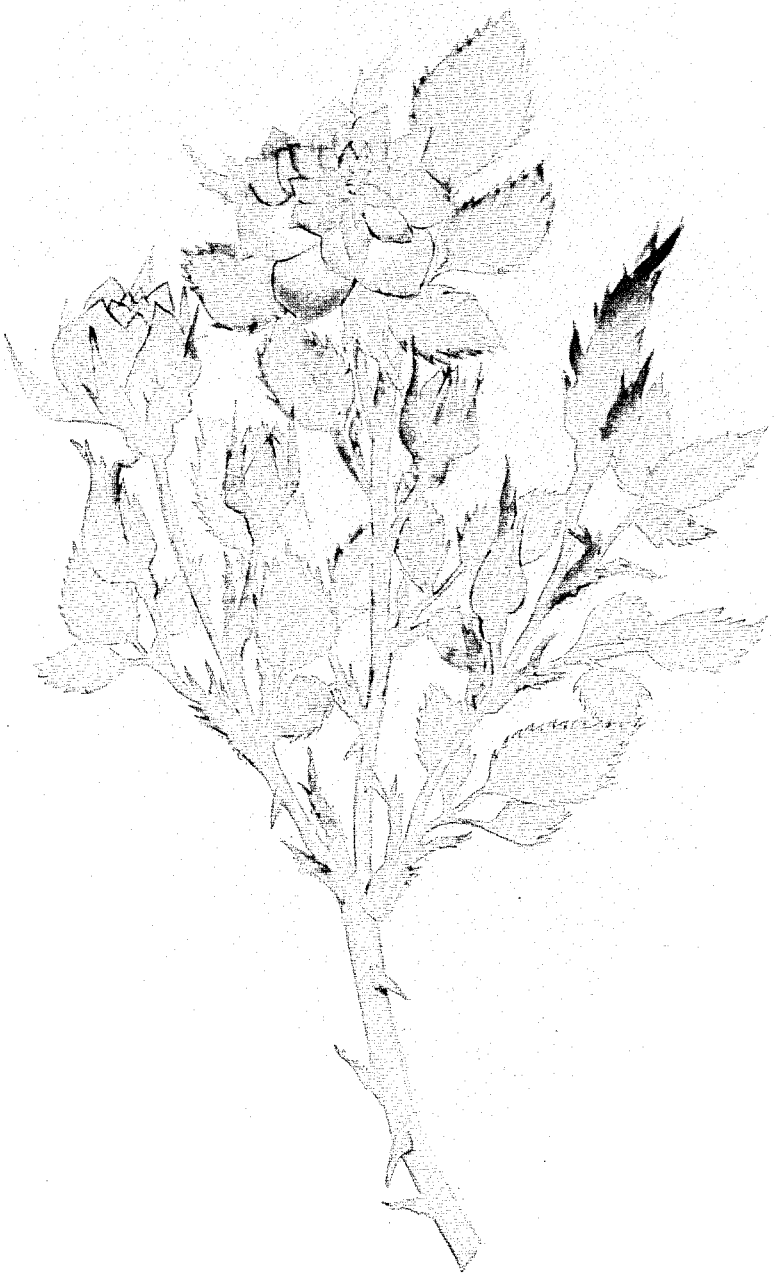
WITNESS
Jeanette Nunn Copley
INVENTOR
Ralph S. Moore United States Patent Office Plant Pat. 2,717
Patented Feb. 21, 1967

2,717
ROSE PLANT
Ralph S. Moore, 2519 E. Mineral King,
Visalia, Calif. 93277
Filed Oct. 11, 1965, Ser. No. 494,992
1 Claim. (Cl. Plt.—6)

The present invention relates to a new and distinct variety of hardy, dwarf, climbing type rose plant of the miniature class; the variety being primarily characterized—as to novelty—by very double red flowers borne in many flowered clusters on short twigs and at the end of new shoots.

The variety is further characterized by:

An abundance of bloom, borne over a long season from spring to frost. Medium to intense fragrance.

A plant which is vigorous, upright with climbing, arching branches, with semi-glossy small foliage with pointed leaflets; the flowers being similar in size and form to Bobolink (U.S. Plant Patent No. 2,009) with a coloring being a brighter red than Bobolink. The plant which has a normal average height of 3½–4 feet at maturity can be easily maintained at a lower height by occasional trimming, if necessary.

A plant which grows and blooms satisfactorily, outdoors for garden use and provides excellent garden decoration as well as flowers for cutting.

The present variety of miniature rose was originated by me in my nursery located at Visalia, California, under conditions of careful control and observation, as a cross between an unknown variety and Magic Wand.

Subsequent to origination of the variety I successfully asexually reproduced it, in my nursery located as aforesaid, by budding as well as cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy, dwarf; climber; seedling; outdoors; cut flowers; garden decoration; shrub.

Class: Climbing miniature.

Flowers:

*Continuity.*—Continuous.

*Fragrance.*—Moderate, pungent fragrance (similar to green tea).

Flowers borne: Several together in medium size clusters (5 to 15 flowers) on normal strength, medium length stems.

Quantity of bloom: Abundant in spring, repeating in lesser quantity until frost.

Bud:

*Peduncle.*—Medium green often tinted bronze; numerous short hairs.

*Before calyx breaks.*—Size—small. Form ovid; pointed; with few foliaceous appendages and numerous tiny short hairs on surface of bud; with foliaceous parts extending beyond the tip of the bud equal to ¼ or more its length.

*Color.*—Medium green tinted reddish or bronze.

*As calyx breaks.*—Color—red (Chrysanthemum Crimson 824/1 to 824/3).

*As first petal opens.*—Slightly deeper red; size—small.

*Form.*—Medium length, ovoid, becoming flat or rounded as it opens.

*Opening.*—Opens well in all weather.

Bloom:

*Size when fully open.*—Small, averaging 1¼".

*Petalage.*—Double to very double—averaging 50 to 80 petals, arranged regularly.

*Form.*—Flat to slightly rounded at first with petals rolled loosely outward, and later at maturity, rounded, with petals being rolled loosely outward.

Petals: Fairly thick; soft; satiny both inside and outside.

*Shape.*—Outside petals broad lanceolate; intermediate—broad lanceolate; inside petals—narrow lanceolate.

*Color.*—Newly opened flower from a plant grown outdoors (Sept. 1965), Visalia, California. Outside petal: outside surface—Chrysanthemum Crimson 824/2 with green-yellow at base; inside surface—Chrysanthemum Crimson 824/2 with yellow at base. Intermediate petal: outside surface—Chrysanthemum Crimson 824/2 with green-yellow at base; inside surface—Chrysanthemum Crimson 824/2 with yellow at base. Inner petal: outside surface—Chrysanthemum Crimson 824/2 with green-yellow at base; inside surface—Chrysanthemum Crimson 824/2 with yellow at base.

*General Color effect.*—Newly opened flower—red. Three days opened—lighter shade of red.

*Behavior.*—Spent petals usually drop off.

*Flower longevity* (Sept. 1965).—on plant in garden—about 5 days. Cut flowers at living room temperature from 3–4 days.

Reproductive organs:

*Stamens.*—Few to average; arranged irregularly about pistil; sometimes mixed with petaloids.

*Filaments.*—Short; yellow.

*Anthers.*—Orange-yellow.

*Pollen.*—Moderate.

*Pistils.*—Few to average.

*Styles.*—Uneven; medium length; bunched; pale greenish white.

*Stigma.*—Pale greenish white.

*Ovaries.*—All enclosed in the calyx.

*Hips.*—None observed.

*Sepals.*—Permanent; spear shaped; recurved.

*Seeds.*—None.

Foliage:

*Leaves.*—Compound of seven leaflets; abundant; small; leathery; semi-glossy.

*Leaflets.*—Shape: lanceolate; apex acute; base rounded acute. Margin: serrate. Color: normal green; new growth often tinted bronze. Rachis: medium strength; upper side smooth, grooved; under side sparsely thorny. Stipules: long; narrow; long, slender points, turning out at an angle of more than 45 degrees.

Growth:

*Habit.*—Climbing; bushy; upright; much branched.

*Growth.*—Free; vigorous.

*Canes.*—Medium; slender.

*Main stems.*—Color: medium green. Thorns: moderately thorny; medium length; hooked slightly downward. Color—medium to dark brown. Prickles: none. Hairs: none.

*Branches.*—Color: medium green. Thorns: moderately thorny; slender; hooked slightly downward; medium oval base. Prickles: none. Hairs: none.

*New shoots.*—Color: medium green often tinted bronze. Thorns: moderately thorny; short; hooked slightly downward; oval base. Prickles: none. Hairs: none.

The miniature rose plant and its flowers as herein described may vary in slight detail due to climatic, soil and cultural conditions under which the variety may be grown; the present description being of the variety as grown at Visalia, California.

The following is claimed:

A new and distinct variety of miniature rose plant of hardy, much branched, upright, climbing type, as illustrated and described, characterized by buds and flowers resembling the Bobolink (Plant Patent No. 2,009) miniature rose in general form but with smaller and better bud form, the color a darker shade of red and the flowers more high centered and slightly smaller; the general color effect being red; and further characterized by a plant which is vigorous, easy to propagate from cuttings, with small semi-glossy foliage and an abundance of bloom, repeating all season from spring to fall, with flowers borne in rather tight, many flowered clusters or sprays.

No references cited.

ABRAHAM G. STONE, *Primary Examiner.*

R. E. BAGWILL, *Assistant Examiner.*